United States Patent
Foster et al.

(10) Patent No.: US 9,604,214 B2
(45) Date of Patent: Mar. 28, 2017

(54) CELL SORTING SYSTEM USING MICROFABRICATED COMPONENTS

(71) Applicant: Owl biomedical, Inc., Goleta, CA (US)

(72) Inventors: John S Foster, Santa Barbara, CA (US); Nicholas C. Martinez, Santa Barbara, CA (US); Daryl W. Grummitt, Santa Barbara, CA (US); Ralf-Peter Peters, Bergisch Gladbach (DE); Christian Peth, Düsseldorf (DE); Markus Nagel, Frechen (DE)

(73) Assignee: Owl biomedical, Inc., Goleta, CA (US)

( * ) Notice: Subject to any disclaimer, the term of this patent is extended or adjusted under 35 U.S.C. 154(b) by 70 days.

(21) Appl. No.: 14/638,495

(22) Filed: Mar. 4, 2015

(65) Prior Publication Data

US 2015/0367346 A1    Dec. 24, 2015

Related U.S. Application Data

(63) Continuation-in-part of application No. 13/998,095, filed on Oct. 1, 2013, now Pat. No. 9,372,144.

(51) Int. Cl.
*B01L 3/00* (2006.01)
*F16K 99/00* (2006.01)
(Continued)

(52) U.S. Cl.
CPC ... *B01L 3/502761* (2013.01); *B01L 3/502738* (2013.01); *B81B 7/00* (2013.01);
(Continued)

(58) Field of Classification Search
CPC ............. B07C 5/34; B01L 3/502715; B01L 3/502738; B01L 3/502746; B01L 3/502753;
(Continued)

(56) References Cited

U.S. PATENT DOCUMENTS

| | | |
|---|---|---|
| 6,838,056 B2 | 1/2005 | Foster |
| 6,941,005 B2 | 9/2005 | Lary et al. |

(Continued)

FOREIGN PATENT DOCUMENTS

| | | |
|---|---|---|
| EP | 2 857 099 | 4/2015 |
| EP | 2 857 100 | 4/2015 |

OTHER PUBLICATIONS

U.S. Appl. No. 13/374,899, filed Jan. 23, 2012, Foster et al.
U.S. Appl. No. 13/374,898, filed Jan. 23, 2012, Foster et al.

*Primary Examiner* — Joseph C Rodriguez
(74) *Attorney, Agent, or Firm* — Jaquelin K. Spong

(57) ABSTRACT

A MEMS-based cell sorter is disclosed, which uses a novel combination of features to accomplish the cell sorting using a microfabricated cell sorting valve housed in a disposable cartridge. The features include an interposer that provides fluid communication between the microfluidic passages in the silicon substrate and a plurality of fluid reservoirs in the cartridge, including a sample, sort and waste reservoir The disposable cartridge may include other features that assist in the handling of small volumes of fluids, such as a siphon region in the sort reservoir and funnel-shaped regions in the sample and waste reservoirs. A mixing mechanism may be provided for stirring the contents of the sample reservoir.

23 Claims, 12 Drawing Sheets

(51) Int. Cl.
  *B81B 7/00* (2006.01)
  *G01N 15/14* (2006.01)
  *G01N 15/10* (2006.01)

(52) U.S. Cl.
  CPC ..... *F16K 99/0046* (2013.01); *G01N 15/1484* (2013.01); *B01L 2200/0652* (2013.01); *B01L 2200/10* (2013.01); *B01L 2300/0654* (2013.01); *B01L 2300/0864* (2013.01); *B01L 2300/12* (2013.01); *B01L 2400/0622* (2013.01); *B01L 2400/0633* (2013.01); *B01L 2400/0644* (2013.01); *G01N 15/1459* (2013.01); *G01N 2015/1006* (2013.01); *G01N 2015/149* (2013.01)

(58) Field of Classification Search
  CPC ..... B01L 2200/0652; B01L 2300/0861; B01L 2300/0864; B01L 2200/027
  See application file for complete search history.

(56) References Cited

U.S. PATENT DOCUMENTS

| | | | |
|---|---|---|---|
| 7,220,594 B2 | 5/2007 | Foster et al. | |
| 7,223,363 B2 * | 5/2007 | McNeely | B01F 5/10 422/417 |
| 7,229,838 B2 | 6/2007 | Foster et al. | |
| 7,264,972 B2 | 9/2007 | Foster | |
| 7,569,789 B2 | 8/2009 | Hayenga et al. | |
| 7,745,221 B2 * | 6/2010 | Butler | B01L 3/502761 422/504 |
| 7,863,035 B2 * | 1/2011 | Clemens | G01N 27/27 417/322 |
| 8,105,849 B2 * | 1/2012 | McDevitt | B01L 3/502715 422/403 |
| 8,120,770 B2 | 2/2012 | Huang et al. | |
| 8,609,039 B2 * | 12/2013 | Zhou | B01L 3/5025 422/500 |
| 8,623,294 B2 * | 1/2014 | Asogawa | B01L 3/50273 422/50 |
| 9,168,568 B2 * | 10/2015 | Foster | B01L 3/502761 |
| 9,404,838 B2 * | 8/2016 | Foster | B01L 3/502761 |
| 2007/0178529 A1 * | 8/2007 | Breidford | B01F 11/04 435/7.1 |
| 2008/0118987 A1 * | 5/2008 | Eastwood | B01L 3/502776 436/166 |
| 2008/0128332 A1 * | 6/2008 | Lean | B01L 3/502761 209/210 |
| 2009/0014360 A1 | 1/2009 | Toner et al. | |
| 2010/0233799 A1 * | 9/2010 | Takayama | G09B 23/12 435/305.2 |
| 2010/0304429 A1 * | 12/2010 | Butler | B01L 3/502761 435/34 |
| 2011/0030808 A1 * | 2/2011 | Chiou | B01L 3/502738 137/13 |
| 2011/0312841 A1 * | 12/2011 | Silverbrook | B01L 3/5027 506/40 |
| 2012/0190104 A1 | 7/2012 | Foster et al. | |
| 2012/0255373 A1 | 10/2012 | Foster et al. | |
| 2014/0034555 A1 | 2/2014 | Foster et al. | |
| 2015/0060303 A1 * | 3/2015 | Blohm | B01L 3/502 205/792 |
| 2015/0177122 A1 * | 6/2015 | Foster | G01N 15/1484 435/309.1 |
| 2015/0328637 A1 * | 11/2015 | Perrault, Jr. | B01L 3/502761 435/287.1 |
| 2016/0040226 A1 * | 2/2016 | Mehta | C12Q 1/6874 506/2 |
| 2016/0158758 A1 * | 6/2016 | Johnson | C12N 5/0081 435/3 |
| 2016/0161392 A1 * | 6/2016 | Ionescu-Zanetti | B01L 3/502738 506/9 |
| 2016/0263575 A1 * | 9/2016 | Foster | B01L 3/502761 |

* cited by examiner

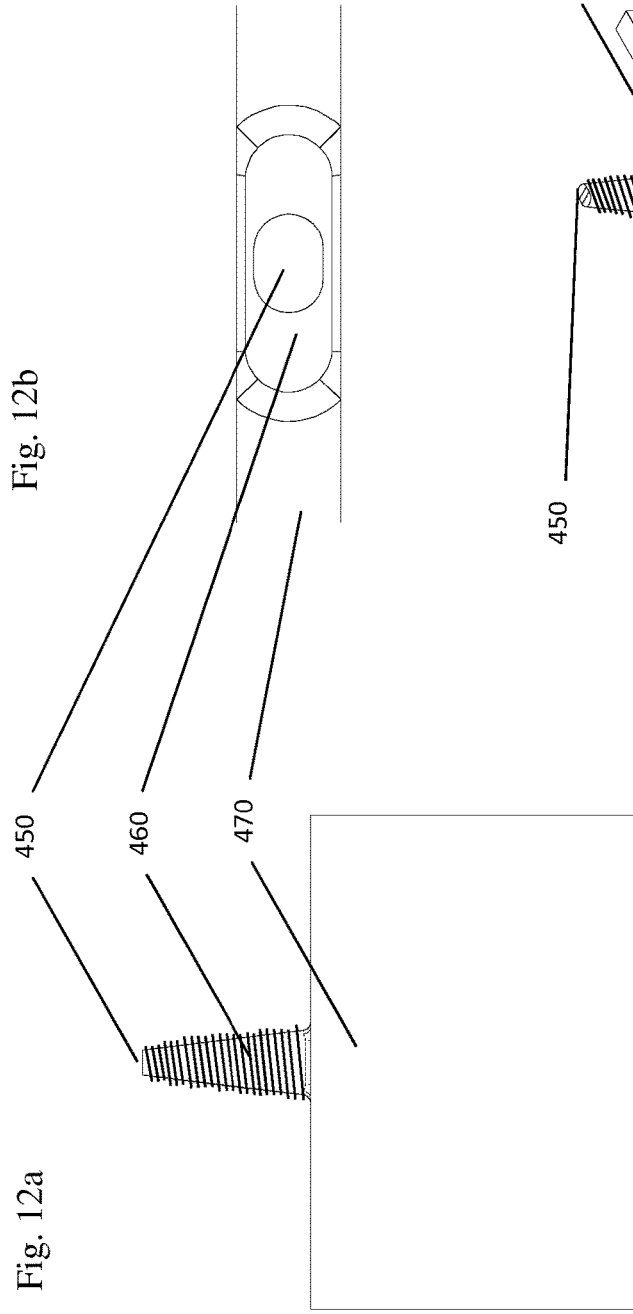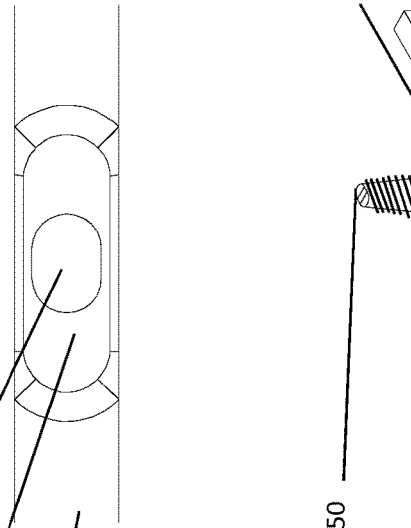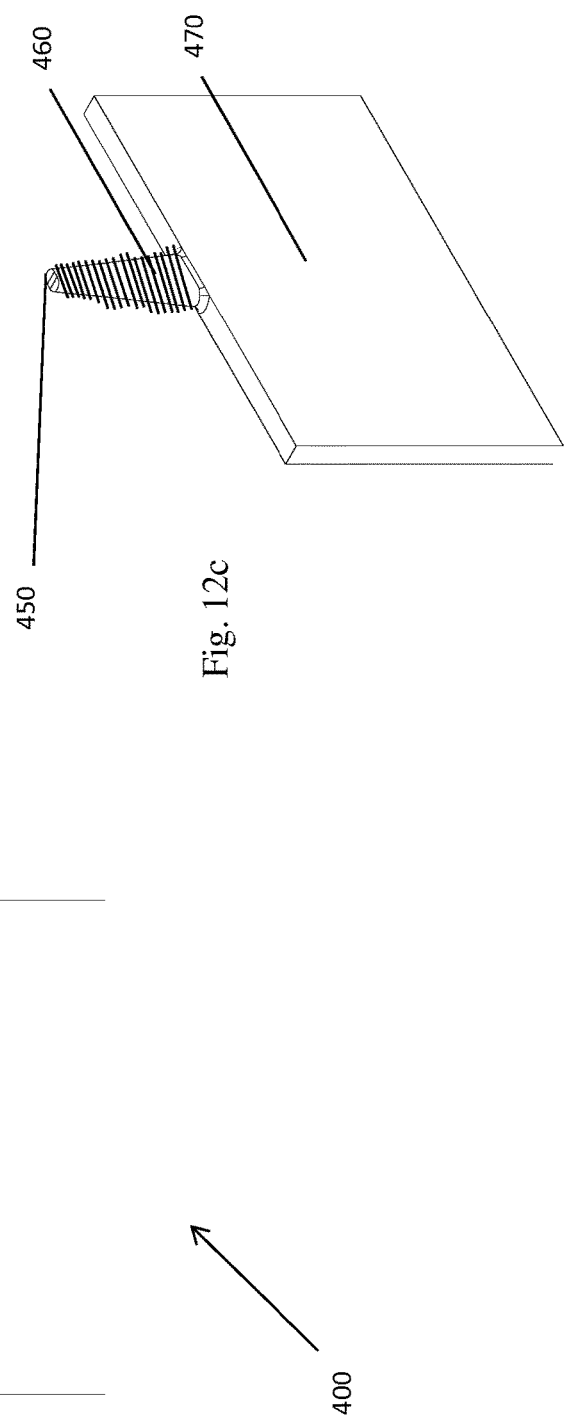

CELL SORTING SYSTEM USING MICROFABRICATED COMPONENTS

CROSS REFERENCE TO RELATED APPLICATIONS

This U.S. Patent Application is a continuation-in-part of U.S. patent application Ser. No. 13/998,095, filed Oct. 1, 2013, which is incorporated by reference herein in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a cell sorting system using a microfabricated, movable cell sorting mechanism.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices can also be made which manipulate particles passing by the MEMS device in a fluid stream.

For example, a MEMS device may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

Previously, particle sorters existed using fluorescence-activated cell sorting (FACS) and are known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between samples, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

MEMS-based cell sorting systems may have substantial advantages over flow cytometers in terms of cost, speed and size. A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b2 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

Among the problems encountered with using microfluidic devices in the cell sorting systems as mentioned above, is the clogging of the narrow passageways, and the interface of these narrow passageways with the macroscopic world, and control of the movement of these very small, movable devices.

SUMMARY

A cell sorting system is described which makes use of a microfabricated cell sorting MEMS chip. The passageways in the MEMS chip are formed lithographically, and are thus very small. Clogging of these narrow passageways presents a significant challenge to reliable, long term operation. Additionally, these narrow passageways must be mated to much larger, macroscopic features, and handle small volumes of fluids, particularly when sorting rare cells.

In the system described here, various novel design elements are brought to bear to enable such a MEMS cell sorting system. The sorting mechanism may be a MEMS fluid valve formed on a silicon substrate, which may be adhered to an interposer and installed in a disposable cartridge. The cartridge may provide all of the fluidic passageways for the handling of the sample fluid, and may include larger reservoirs (e.g. sort, sample and waste reservoirs) for the storage of volumes of fluids. A plastic interposer may be used to provide the interconnections between the microscopic passages of the MEMS fluid valve and the macroscopic features of the reservoirs. The MEMS fluid valve, interposer and reservoirs may all be contained in a disposable cartridge, such that sterilization of the cell sorting system is straightforward, the cartridge is simply disposed of.

A specially designed electromagnet may provide the precisely located electromagnetic fields which cause the very small MEMS chip to move within the much larger system. This electromagnet minimizes heat produced, and thus improves efficiency. Finally, a special formulation of fluid materials is used to reduce or eliminate clogging.

The disposable cartridge and interposer may include a number of novel features, such a s a mixer, and funnel-shaped regions that may assist in the handling of small volumes of fluids. The mixer may be submerged in the sample reservoir, thereby allowing mixing of the contents. Funnel-shaped regions may be provided in the sort reservoir, the sample reservoir, and the waste reservoir, for the collection of small volumes of fluids.

Accordingly, a cell sorting system is described, which may include a cell sorting valve microfabricated on a silicon substrate with microfabricated channels leading from the cell sorting valve, a disposable cartridge containing a sample reservoir, a sort reservoir and a waste reservoir and an interposer that that provides fluid communication between the microfabricated channels in the silicon substrate and the reservoirs in the disposable cartridge. The cell sorting system may further include an electromagnet with a tapered tip, coils and magnetic core, wherein the tapered shape serves to concentrate the lines of flux produced by the coils and core, and exit from the electromagnet in the vicinity of the tip. Finally, a cation-independent DNAse may be used as a buffer in which to suspend the target particles, reducing or eliminating clogging of the small channels in the device.

BRIEF DESCRIPTION OF THE DRAWINGS

Various exemplary details are described with reference to the following figures, wherein:

FIG. 12a is a plan view of the targeted electromagnet that may generate the magnetic field which may actuate the MEMS chip sorter from the first position (FIG. 1) to the second position (FIG. 2); FIG. 12b is a closeup view of the magnet tip; FIG. 12c is a perspective view of the targeted electromagnet;

It should be understood that the drawings are not necessarily to scale, and that like numbers may refer to like features.

DETAILED DESCRIPTION

Systems and methods are described for sorting target particles from non-target materials in a fluid stream. The systems and methods make use of a microfabricated (MEMS) movable valve or sorting mechanism, which directs the target particle from a sample input passageway into a sort passageway, while allowing non-target material to flow into a waste passageway. Both the sort and waste passageways lead to a separate, respective reservoir, the sort and the waste reservoir, and are stored there until removal. The sort, sample and waste reservoirs, along with the MEMS chip sorter, may be contained in a plastic disposable cartridge. This cartridge may then be discarded after the fluids are collected from the reservoirs. This allows greatly reduced burden for sterilizing the system between samples. The systems and methods may also have significant advantages in terms of cost, performance, speed and complexity. The system may also be substantially gentler in its handling of cells, such that viability of cells in the effluent is greatly improved compared to droplet-based flow cytometers.

Because of the microfluidic nature of this cell sorting system, measures are taken to reduce or eliminate clogging, and to handle the small volumes of fluids, and to control the very small movable valve. An interposer may be used to provide the interconnections between the microscopic passages and the macroscopic features. Finally, specially designed electromagnet provides the precisely located electromagnetic fields which cause the very small MEMS chip to move within the much larger system. This electromagnet minimizes heat produced, and thus improves efficiency. Each of these features is described further below.

Figure 1:
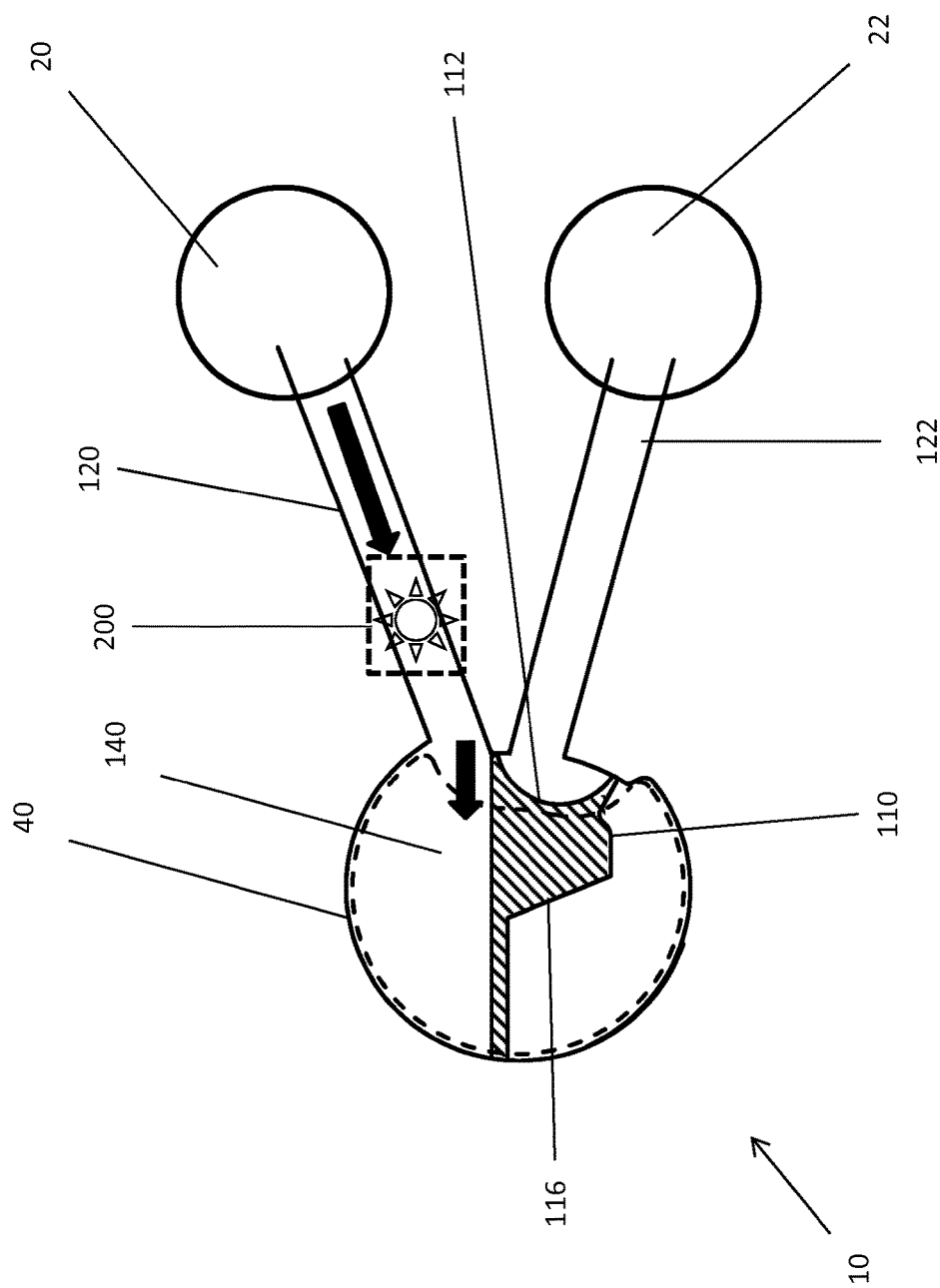
FIG. 1 is a schematic illustration of a MEMS chip sorter in a first position.

FIG. 1 is a schematic diagram of a microfabricated cell sorting mechanism, MEMS chip sorter 10, which may be used in the particle sorting system described here. Details of cell sorting mechanism may be found in co-pending U.S. patent application Ser. No. 13/998,095, (hereinafter the '095 patent application) incorporated by reference herein. Among the unique features of microfabricated cell sorting mechanism 10 is that the motion of the cell sorting valve 10 is parallel to the fabrication plane of the valve. In addition, the waste channel 140 is substantially orthogonal to the sample inlet channel 120 and the sort output channel 122. These features enable distinct advantages in terms of speed and precision, valve throughput and ease of the microfluidic sorting.

It should be understood that the term "chip sorter" 10 is an abbreviated term for a microfabricated cell sorting valve 10, as a "chip" is a device microfabrucated on a substrate. Either term is intended to designate a microfabricated movable valve formed on a surface of a substrate, using MEMS fabrication techniques, which, by its movement, is capable of separating target particles from non-target material.

In the plan view illustration of FIG. 1, the novel MEMS chip sorter or cell sorting valve 10 is in the quiescent (un-actuated) position. The chip sorter 10 may include a microfabricated fluidic valve or movable member 110 (hatched area) and a number of microfabricated fluidic channels 120, 122 and 140. Microfabricated fluidic channel 140 (shown as dashed area 140 in FIG. 1 and FIG. 2) serves as output channel and is may be located directly below at least a portion of the microfabricated member 110 and is not parallel to the plane of the microfabricated fluidic channels 120, 122 or the microfabricated member 110. Microfabricated member 110 is fabricated and moves in a path parallel or within this plane. Preferably, the microfabricated fluidic channel 140 is orthogonal to the plane of the microfabricated fluidic channels 120, 122 and the path of motion of microfabricated member 110. The aperture of microfabricated fluidic channel 140 may cover preferably overlap at least a portion of the path of motion of microfabricated member 110, i.e. the dashed, area overlaps the microfabricated member 110 over at least a portion of its motion, as shown in FIG.

Figure 2:
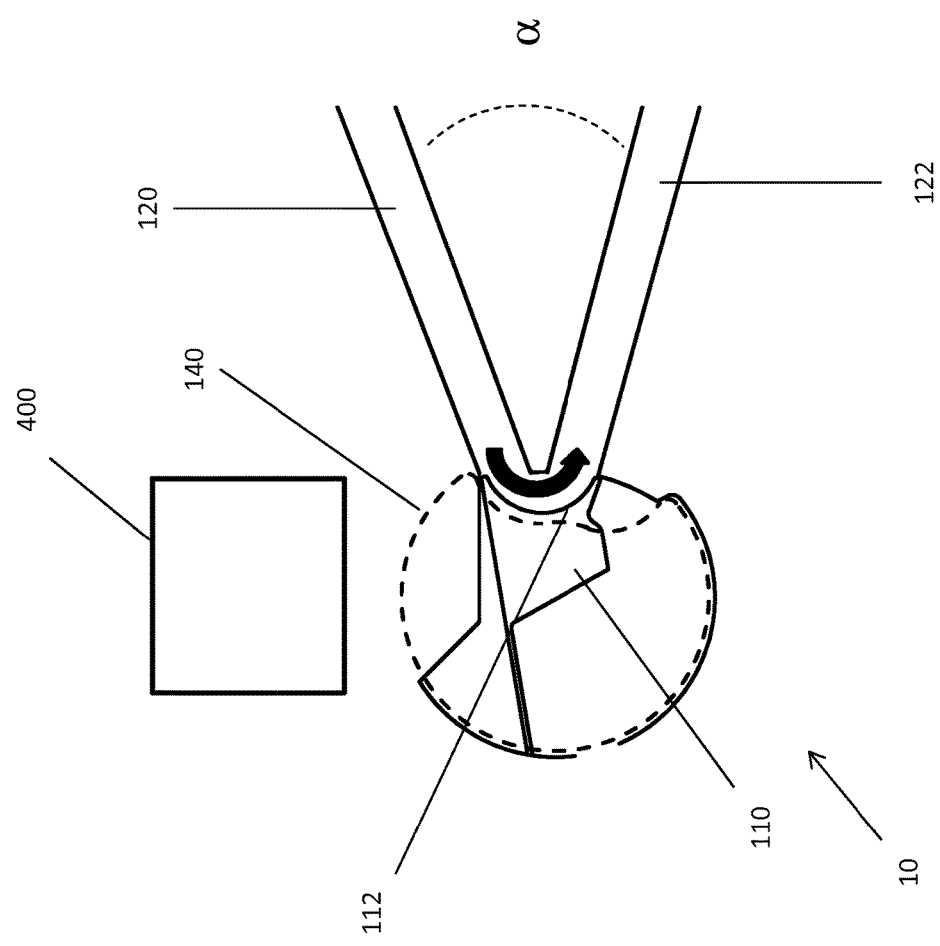
FIG. 2 is a schematic illustration of a MEMS chip sorter in a second position.

1 and FIG. 2. This overlap may allow a fluid path to exist between the input channel 120 and the output channel 140 when the microfabricated member is in the "waste" or unactuated position (FIG. 1), and this path is closed off and the particles redirected in the "sort" or actuated position (FIG. 2). As described previously, this architecture may reduce the fluid resistance, thereby increasing the speed of microfabricated member 110.

The movable member 110 and microfabricated fluidic channels 120, 122 and 140 may be formed on the surface of a suitable substrate, such as a silicon substrate, using MEMS lithographic fabrication techniques as described in greater detail in the '095 application. The fabrication substrate may have a fabrication plane in which the device is formed and in which the movable member 110 moves.

A sample stream may be introduced to the microfabricated movable member 110 by a sample inlet channel 120. The sample fluid may be stored in a sample reservoir 20 prior to sorting by movable member 110. The sample stream may contain a mixture of particles, including at least one desired, target particle and a number of other undesired, non-target particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline, or the novel chemistry described below. The inlet channel 120 may be formed in the same fabrication plane as the movable member 110, such that the flow of the fluid is substantially in that plane. The motion of the cell sorting valve 10 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Laser interrogation region 200 is the portion of the microfluidic passageway in which an illuminating or interrogating laser is directed on the target particle, in order to distinguish it from the other constituents of the fluid sample. Details as to this detection mechanism are well known in the literature, and further discussed below with respect to FIG. 3. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an non-target particle and thus rejected or otherwise disposed of.

With the movable member 110 in the position shown, the input stream passes unimpeded to a waste outputchannel 140 which is out of the plane of the inlet channel 120, and thus out of the fabrication plane of the MEMS chip sorter 10. That is, the flow is from the inlet channel 120 to the output orifice 140, from which it flows substantially vertically, and thus orthogonally with respect to the inlet channel 120. This output orifice 140 leads to an out-of-plane channel that may be perpendicular to the plane of the paper showing FIG. 1. More generally, the waste output channel 140 is not parallel to at least one of the plane of the inlet channel 120 or sort channel 122, or the fabrication plane of the movable member 110. In one embodiment, the sort and sample channels may be antiparallel, that is, flow in the sort channel is in an opposite direction to flow in the incoming sample channel.

Accordingly, the cell sorting system may include a cell sorting valve 10, which directs the target particles from a sample channel 120 into a sort channel 122 formed in the silicon substrate and the non-target material from the sample channel 120 to a waste output channel 140 also formed in the silicon substrate. The cell sorting valve 10 may also move in a plane parallel to the surface, and direct the target particles from the sample channel 120 into the waste channel 140 when the microfabricated cell sorting valve 10 is in a first position, and which directs the other particles into the sort channel 122 when in a second position, wherein the sort channel 122 and the waste channel 140 are substantially antiparallel, and the sample channel 120 and waste channel 140 are substantially orthogonal.

The waste output channel 140 may have an orifice, which may be a hole formed in the fabrication substrate, or in a covering substrate that is bonded to the fabrication substrate. Further, the movable member 110 may have a curved diverting surface 112 which can redirect the flow of the input stream into a sort output stream. The contour of the surface 112 may be such that redirects the sample stream from the inlet channel 120 into the sort channel 122 in one position, while allowing it to flow to the waste output channel 140 in another position. Accordingly, by having the surface 112 overlap the inlet channel 120, a route exists for the input stream to flow directly into the waste output channel 140 when the movable member 110 is in the un-actuated waste position, as is shown in FIG. 1. The waste output channel 140 may lead to a waste reservoir 40, which may collect the non-target material. The inlaid magnetically permeable material 116 on the movable member 110 may cause its movement, and will be described below in the description of FIG. 2.

FIG. 2 is a plan view of the MEMS chip sorter 10 in the actuated position. In this position, the movable member 110 or valve 10 is deflected upward into the position shown in FIG. 2. The curved diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle □ between the inlet channel 120 and the sort channel 122. This angle may be any value up to about 90 degrees. Actuation of movable member 110 may arise from a force from force-generating apparatus 400, shown generically in FIG. 2. In some embodiments, force-generating apparatus 400 may be an electromagnet, as described above. However, it should be understood that force-generating apparatus may also be electrostatic, piezoelectric, or some other means to exert a force on movable member 110, causing it to move from a first position (FIG. 1) to a second position (FIG. 2). The sort channel 122 may lead to a sort reservoir 22 which collects the sorted, target particles as effluent from the movable valve in the position shown in FIG. 2. The inlet channel 120 may conduct the sample fluid from an sample reservoir 20 to the waste channel 140 and waste reservoir 40 as was shown in FIG. 1, or to the sort channel 122 and sort reservoir 22, as shown in FIG. 2.

In some embodiments, the force generating apparatus 400 may include coils which generate a magnetic field, which then interacts with the movable member 110. In order to make the movable member 110 responsive to such an electromagnetic force, it may have a magnetically permeable material inlaid into movable valve 110. The extent of this inlaid magnetic material 116 may be just inside the edge of the outline of the movable member 110 as shown by the dashed lines in FIGS. 1 and 2.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000. Accordingly, movable member 110 may have permalloy material inlaid 116 into the movable member 110 and subsequently planarized so that the profile of the movable valve remains flat. Additional details as to the fabrication of such permeable features may be found in the incorporated '095 patent application.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux. A novel core design is described below with respect to FIG. 10a-10c, which concentrates the lines of flux in a very specific area, to optimize the control over the movable member 110.

It should be understood that the magnetostatic embodiment described above is but one of a number of actuation mechanisms that can be used to move the cell sorting valve or chip sorter 10. More generally, the cell sorting system may be constructed with a cell sorting valve 10, wherein when the cell sorting valve 10 is in a first position, a passage between the sample channel 120 and the waste channel 140 is formed. When the cell sorting valve 10 is in the second position, a passage between the sample channel 120 and the sort channel 122 is formed. The cell sorting valve 10 may move from the first position to the second position in response to the application of a force, and that force may be at least one of mechanical, electrostatic, magnetostatic, piezoelectric and electromagnetic. In the electrostatic embodiment, a permeable magnetic material is inlaid in the movable member of the microfabricated cell sorting valve 10, and a source of magnetic flux 400 is provided. The magnetic flux interacts with the inlaid permeable magnetic material 116 to move the microfabricated cell sorting valve 10, whereby the microfabricated cell sorting valve moves from the first position to the second position when the source of magnetic flux 400 is activated.

Figure 3:
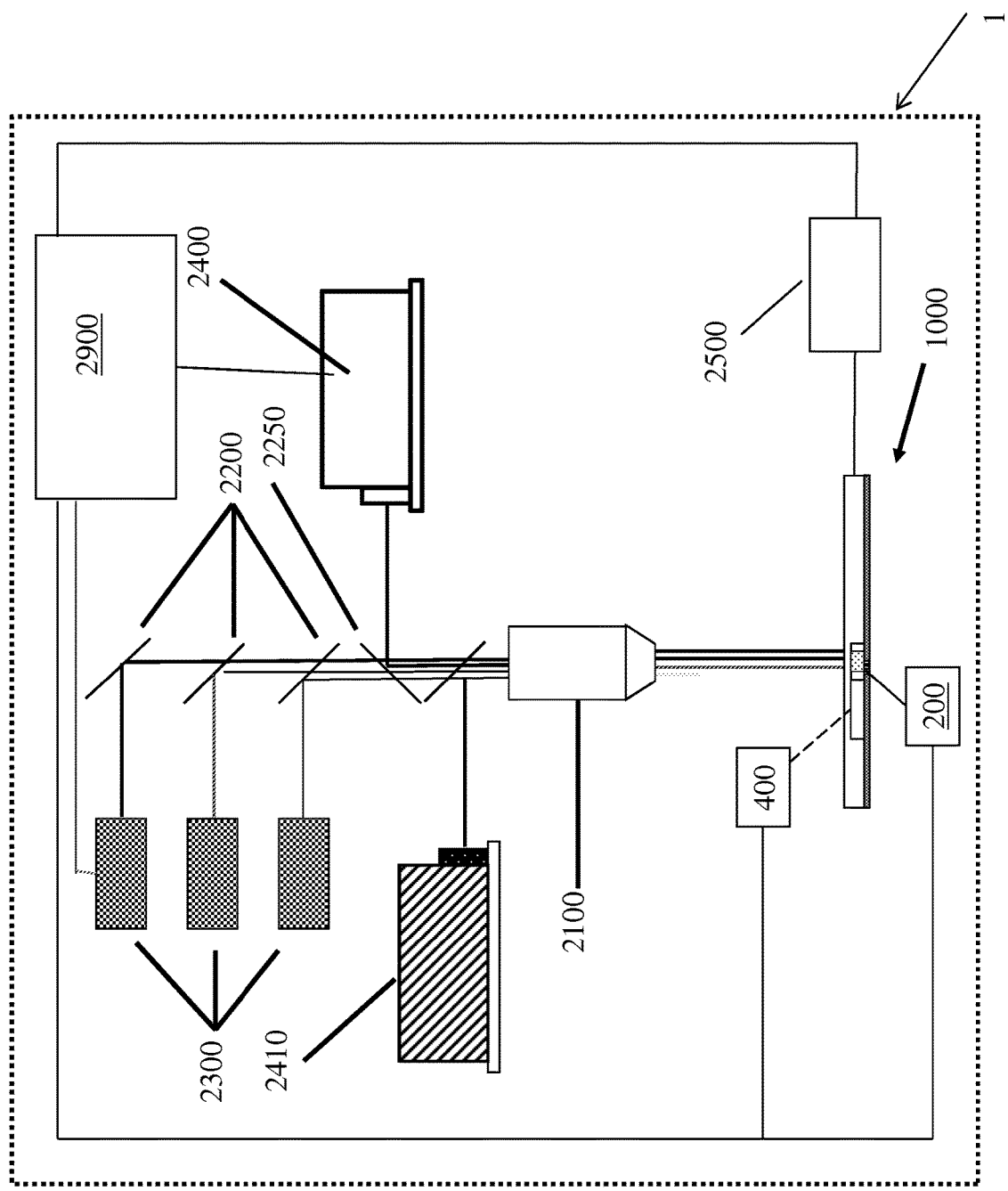
FIG. 3 is a schematic illustration of an exemplary MEMS cell sorting system which may make use of the MEMS sorter of FIGS. 1 and 2.

FIG. 3 is a schematic illustration of the cell sorting system 1 which may use microfluidic passageways, a MEMS chip sorter 10 housed in a disposable cartridge 1000, and a flux-generating apparatus 400. What follows is a description of some other components of the system and how they interact with the MEMS chip sorter 10. In particular, FIG. 3 lays out the optical path of the interrogating laser for interrogation region 200, and the control of fluid flow in channels 120-140 and control of MEMS chip sorter 10. After the system level description, the discussion will turn to the unique features of system 1 that allow the microfluidic system 1 to work in a precise, reliable and predictable way.

As shown in FIG. 3, the microfabricated MEMS chip sorter 10 may be housed in a disposable cartridge 1000, which may be loaded onto a movable stage and oriented with respect to detection optics 2100 and interrogating lasers 2400 in the cell sorting system 1. Fluid then flows through the MEMS chip sorter 10 from fluid reservoirs also housed in disposable cartridge 1000 through a series of passageways as will be described below with respect to FIGS. 4-9.

In the normal operation of system 1, the target particle may be a particular cell, such as a stem cell, or a cancer cell, which has been tagged with a fluorescent marker. This marker emits photons having a particular energy when irradiated with a laser 2400 operating at a predefined wavelength. Accordingly, in this cell sorting system, a laser source 2400 may be directed by a turning mirror 2250 through the detection/collection optics 2100 to the laser interrogation region 200 that was shown in FIGS. 1 and 2. The optical axis of the detection/collection optics 2100 and the laser source 2400 may be collinear, at least over a portion of the optical path. Thus, the orientation of the laser application and optical detection along this optical axis may be perpendicular or orthogonal to the substrate fabrication plane, orthogonal to the plane of motion of the movable valve 110 and orthogonal to the flow of the sample fluid through the detection region.

The fluorescence emitted from the irradiated particles may be shaped by detection/collection optics 2100 and separated by dichroic mirrors 2200 and directed into a bank of photodetectors 2300. A plurality of photodetectors may accommodate multiple wavelengths of emitted light, for multiparametric detection. The signal output by the photodetectors 2300 indicates the presence or absence of the target particle in the laser interrogation region 200. The signal may be delivered to a controller 2900, which manages the relative timing of the components in the particle sorting system 1, and collects the data. The controller 2900 may be a general purpose computer or a specialized circuit or ASIC. Upon detection of the target particle, a signal is generated by the controller 2900 which energizes the force-generating or flux-generating apparatus 400. The controller 2900 may also provide the fluidic control to the MEMS chip sorter 10, via one or more pneumatic, hydraulic, piston-based or mechanical force-based mechanisms which are illustrated generically by fluid control means 2500. The rate at which particles are detected may be monitored by the controller 2900, which may maintain the fluid control means 2500.

The force generating apparatus 400 is a device which causes a force to arise in the movable member 110 itself, causing the motion of the movable member. This force-generating apparatus 400 may not be directly mechanically coupled to the MEMS particle manipulation device 10, as indicated by the dashed line in FIG. 3. For example, the force-generating apparatus 400 may be a source of magnetic flux which causes a magnetostatic force to arise in an inlaid permeable material 116 in the MEMS movable member 110 of the cell sorting valve 10 as described previously. Accordingly, flux generating apparatus 400 may be an electromagnet with a magnetic core and windings. This force may pull the movable member 110 toward the force-generating apparatus 400, opening the sort channel 122 and closing the waste channel 140, as was shown in FIGS. 1 and 2.

Importantly, the force-generating apparatus 400 may reside in the particle sorting system 1, rather than in the MEMS chip sorter 10. As mentioned previously, this may reduce the cost and complexity of the MEMS chip sorter 10, which may be housed in the disposable portion 1000 of the system 1. In the compact system shown in FIG. 3, it is important that excessive heat not be generated by force-generating apparatus 400. As mentioned previously, because of the very small size of MEMS chip sorter 10, force-generating apparatus 400 may also need to generate lines of flux which are concentrated in a small area. Details as to the design of a novel flux-generating apparatus 400 which may be suitable in this application are discussed below with respect to FIGS. 10a-10c.

Another optional laser 2410 may also be included to provide a second optical channel in cell sorting system 1.

As mentioned, laser interrogation region 200 is the portion of the microfluidic passageway in which the laser 2400 is directed on the target particle, in order to distinguish it from the other constituents of the fluid sample.

Upon passing through the detection region 200, a signal is generated by the detector 2300 indicating that a target particle is present in the interrogation region 200. After a known delay, a signal is generated by the controller 2900 which indicates that the sorting gate, i.e. the movable member 110 of the cell sorting valve 10 is to be opened, in order to separate the target particle which was detected, from the other components in the fluid stream. The movable member 110, of the MEMS valve 10 may comprise permeable magnetic materials 116 as mentioned previously, so that the magnetic force may arise in it in the presence of a magnetic field. When the signal is generated by the controller 2900, a force arises in the embedded magnetically permeable material 116 which draws the movable valve 110 toward the force generating apparatus 400. This motion may close off waste channel 140 and redirect the target particle into a sort channel 122. The sorted sample is subsequently collected from a sort reservoir at the end of the sort channel 122, which holds the sorted sample. As mentioned previously, the controller 2900 may also control flow rates based on the rate at which sorting events are recorded.

A fluid control means 2500 may control the direction and velocity of fluid flowing through the channels of the MEMS chip cell sorting valve 10. The fluid control means 2500 may be controlled based on a number of criteria as described below. The fluid control means 2500 may include pneumatic, hydraulic, and/or one way valves, and/or may include a piston or a pump and associated fluidic passages. During normal operation, the flow may be controlled by the fluid control means 2500 in a feedback loop with controller 2900 to keep cell velocity, fluid pressure, or event rate constant, for example.

In a further embodiment, the cell sorting system 1 may comprise a feedback loop to prevent clogging of the channels by cells or other solid material suspended in the fluid. Biological cells especially tend to adhere at the channel surfaces, edges or offsets, thereby reducing the flow of liquid through the system and/or overall cell sorting performance. The feedback loop may consist of at least the fluid control means 2500 such as a pump and the controller 2900.

The controller 2900 may detect impending clogging by monitoring the fluid pressure and/or the cell velocity within the system. If the fluid pressure and/or the cell velocity fall below a predefined threshold, it may be indicative of impending clogging. The controller 2900 may increase the pump rate until the fluid pressure and/or the cell velocity reaches the threshold again. The fluid pressure can be monitored by an appropriate detector, and cell velocity can be deduced by monitoring the event rate in the optical channel. Preferably, the cell speed may be between 0.2 and 10 m/s, and may be constant within +/−0.2 m/s. Accordingly the threshold activating the feedback loop may be a reduction of cell speed by around 0.2 m/s or the equivalent in loss of pressure. It should be understood that the details given here are exemplary only, and that the selection of such operating parameters will depend on the specifics of the application.

At the end of a sorting operation when the volume of sample to be sorted in nearly exhausted, the controller 2900 in concert with the fluid control means 2500 may reverse the flow of fluid in the microchannels, thus keeping the passages wet, as described in U.S. patent application Ser. No. 14/167,566, filed Jan. 29, 2014 and incorporated by reference in its entirety. The system 1 may also have the means to evaluate the effectiveness of the sorting process by reversing the flow through the laser interrogation region 200, as described in detail in U.S. patent application Ser. No. 13/104,084, filed Dec. 12, 2013 and incorporated by reference in its entirety.

Accordingly, the cell sorting system 1 described here may include an interrogation means 200 comprising a laser in a laser-based, induced fluorescence system, wherein a fluorescent tag is affixed to a target particle, and emits a fluorescent signal when irradiated by the laser. The system may include a disposable cartridge 1000 which is configured to be accepted into the cell sorting system 1 on a positionable stage, on which it can be positioned with respect to at least one laser source 2400, and at least one optical detector 2300. The cell sorting system 1 may further include a computer 2900 which is in communication with the at least one laser source 2400, at least one optical source 2100 and the cell sorting valve 10, to separate the target particles from the non-target material.

What follows is a description of the enabling aspects of MEMS cell sorting system 1, in particular, what aspects allow the fluid to flow to and from MEMS chip sorter 10 in a repeatable and reliable way, from macroscopic reservoirs to the MEMS chip sorter 10, and to control the very small MEMS chip sorter 10.

Figure 4:
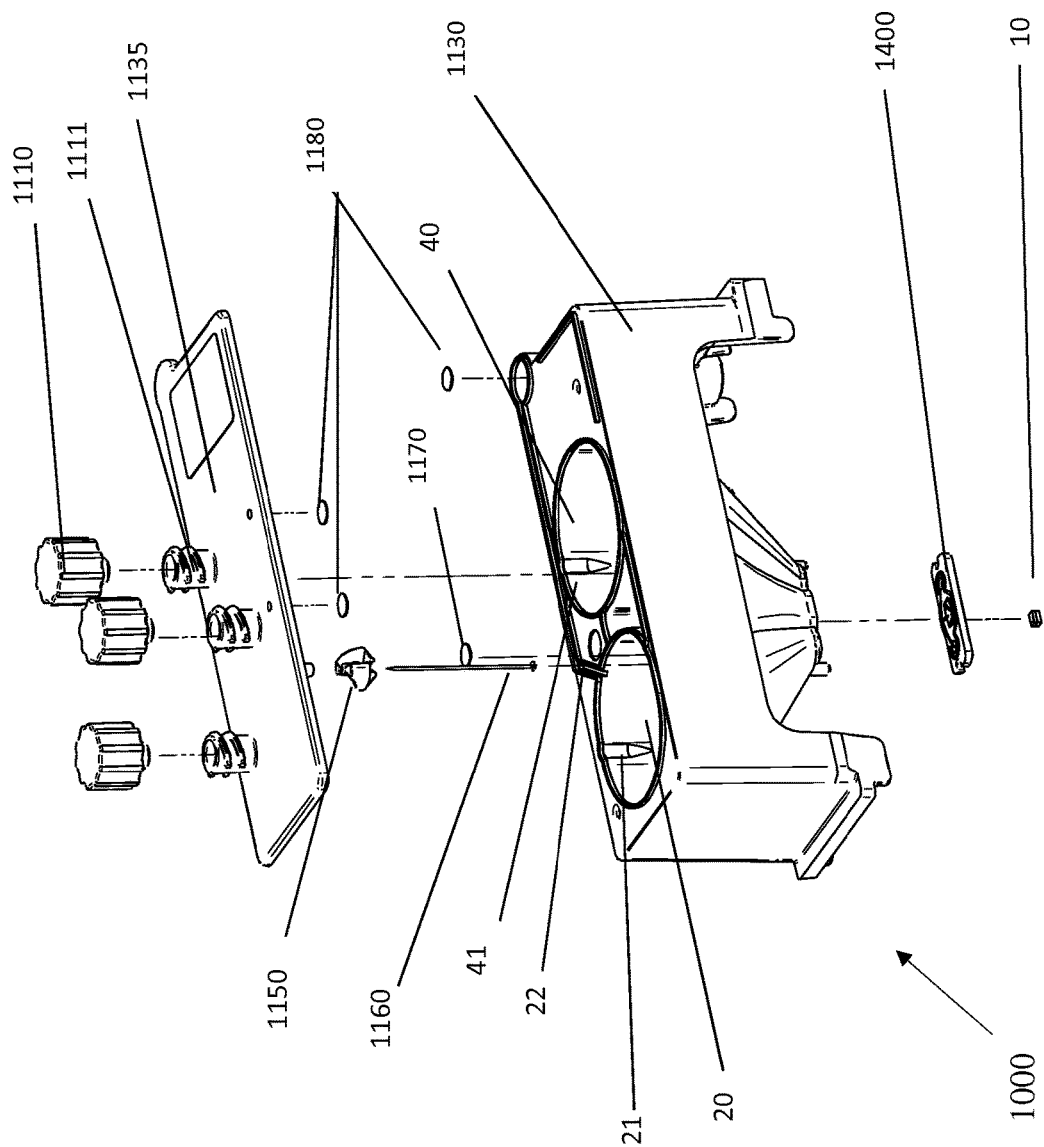
FIG. 4 is an exploded view of an exemplary disposable cartridge which may be used in the MEMS cell sorting system of FIG. 3, which includes a MEMS chip sorter and an interposer.

FIG. 4 is an exploded perspective view of an exemplary disposable cartridge 1000 which may be used in the particle sorting system shown in FIG. 3. Disposable cartridge 1000 may include several assemblable pieces, such as top 1135 and base 1130.

Disposable cartridge 1000 may house MEMS chip sorter 10 and provide storage in fluid reservoirs. Accordingly, the base 1130 of disposable cartridge 1000 may have a plurality of voids or compartments formed therein, including sample reservoir 20, sort reservoir 22 and waste reservoir 40. As described further below, the sample to be sorted may be stored in sample reservoir 20, the sort effluent in sort reservoir 22 and waste effluent in waste reservoir 40. The fluidic passageways between these voids may all be disposed in the interposer 1400 and/or in the MEMS chip sorter 10. Accordingly, the interposer 1400 may provide a sort fluid path between a sort reservoir 22 in the disposable cartridge and the sort channel 122 in the silicon substrate, a waste fluid path between a waste reservoir 40 in the disposable cartridge and the waste channel 140, and a sample fluid path between the sample channel 120 and a sample reservoir 20.

It should be understood that the term "sort" fluid, "sort" sample or "sort" reservoir may refer to a collection of target particles. The "waste" fluid, "waste" sample or "waste" reservoir may refer to a collection of non-target materials in the fluid stream. Other equivalent language is "positive fraction" to refer to the sort sample, and "negative fraction" to refer to non-target material. Accordingly, in the text below, "sort" portion may be equivalent to the "positive fraction" and refer to a collection of target particles, and "waste" may refer to the negative fraction and to a collection of non-target materials.

Between the top 1135 and the base 1130 may be disposed a number of filters 1180 to protect the sample from contamination or debris. These filters 1180 may be 0.20 micron Sterifilters, for example. The filters 1180 may be located directly above the various fluid reservoirs 20, 22 and 40. There may also be in-line filters within the fluid channels, which are for catching debris in the fluid and may be about 20 microns in pore size.

The sample reservoir 20, sort reservoir 22 and the waste reservoir 40 may also include funnel-shaped features that allow the handling of small volumes of fluids. The sort reservoir 22 may contain a siphon-like structure that is described below with respect to FIG. 7, where it is illustrated in greater detail. However, the sample reservoir 20 and waste reservoir 40 may also contain features which assist small volume handling. This feature may be a contoured surface. A funnel-shaped feature should be understood to mean a generally conical structure that is shaped to collect small volumes of fluid running down the wall of the reservoir, Both the sample reservoir 20 and the waste reservoir 40 may include such funnel-shaped features, 21 and 41 respectively. Thus, the cell sorting system 1 described here may include a sample reservoir 20 and waste reservoir 40, wherein the sample reservoir 20 further comprises a funnel-shaped feature 21 formed in the wall of the sample reservoir 20, which collects smaller volumes of sample fluid, wherein the smaller volume of sample fluid is less that about 10% of a total fluid volume of the sample reservoir 20. Similarly, the waste reservoir 40 may further comprise a funnel-shaped feature 41 formed in the wall of the waste reservoir 40, which collects smaller volumes of waste fluid, wherein the smaller volume of waste fluid is less that about 10% of a total fluid volume of the waste reservoir 40.

Within the sample reservoir 20 and enclosed between the top 1135 and the base 1130 may be a magnetized propeller 1150, and a needle 1160 which may act as a shaft for magnetized propeller 1150. Upon exposure to a circulating magnetic field, magnetized propeller 1150 may rotate on shaft 1160, causing the contents of the sample reservoir 20 to be mixed or homogenized. Finally, a 0.20 micron filter 1170 may be placed over the sort reservoir 22, to protect the sorted contents from contamination from the ambient environment. Alternatively, the propeller 1150 may be driven directly by a mechanical coupling to a small motor, which may cause the rotation of the propeller 1150 and thus the mixing of the contents of the sample reservoir 20. Details of the construction of the mixing elements may be shown in more detail in FIG. 6, and discussed below with respect to that figure.

Sample fluid may be introduced to the sample reservoir 20 with a pipette, or with a syringe and plunger (not shown) through the access ports 1111 shown, whereupon the cartridge 1000 may be sealed with male leur lock sealing elements 1110. Alternative sealing techniques may also be used, such as thumbscrews. Alternatively, the cartridge 1000 may be delivered with the sample fluid already loaded therein.

Figure 5:
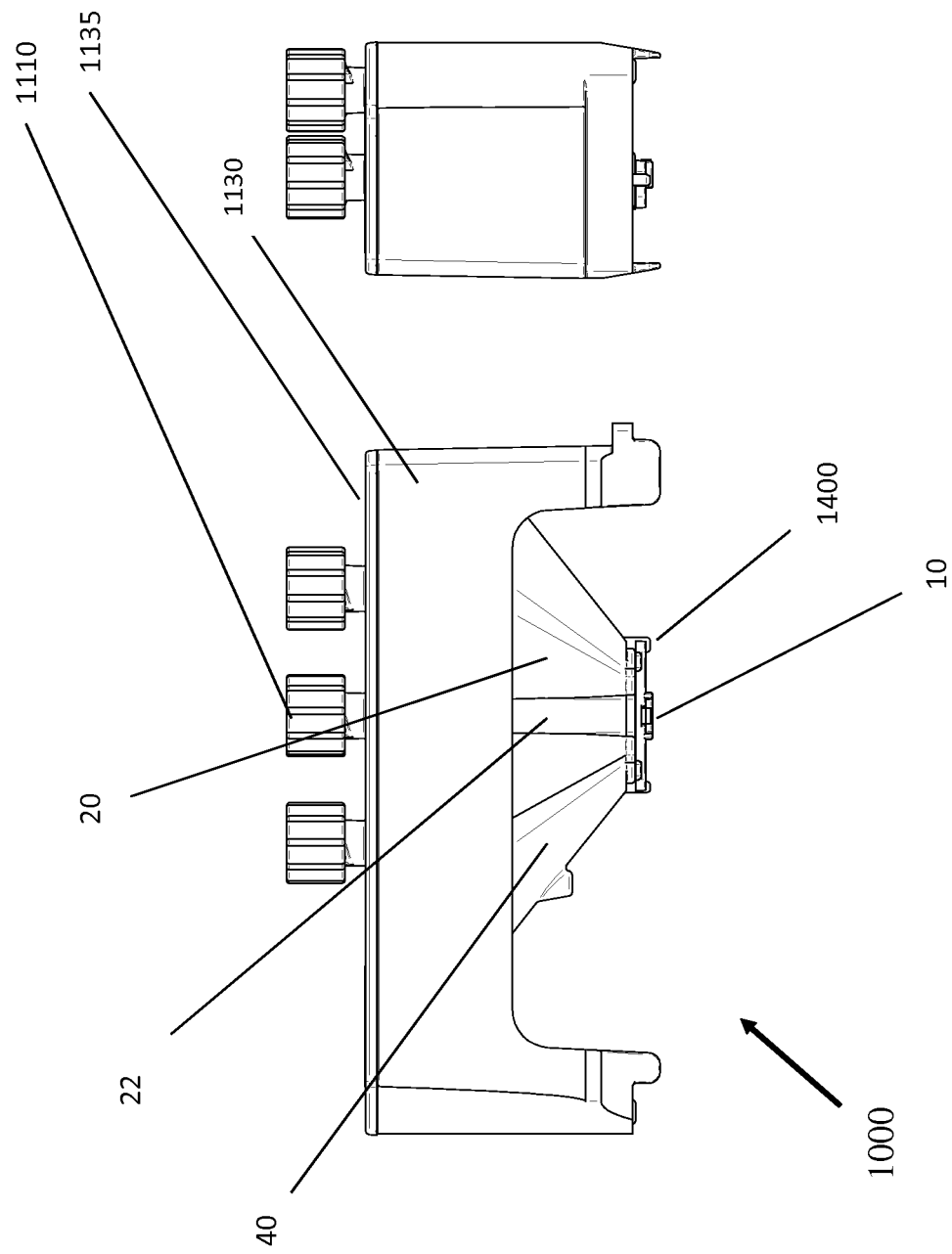
FIG. 5a is a side view of the exemplary disposable cartridge which may be used in the MEMS cell sorting system of FIG. 3, which includes a MEMS chip sorter and an interposer.
FIG. 5b is an end view of the exemplary disposable cartridge.

FIG. 5 is a side view of the assembled disposable cartridge 1000, showing the sample reservoir 20, sort reservoir 22 and waste reservoir 40. Shown in the assembled view are the relative locations of the MEMS chip sorter 10 and interposer 1400 with respect to the cartridge base 1130. It should be noted that FIG. 5 is inverted compared to FIG. 4, such that the sample reservoir 20, shown on the left hand side of the cartridge in FIG. 4, is now located on the right hand side in FIG. 5, as are the associated channels, stirrer, etc.

To provide a transition region between the very fine, microfabricated features of the MEMS chip sorter 10 and the much larger fluid volumes of reservoirs 20, 22 and 40, an interposer 1400 may be provided. The interposer 1400 may be formed from plastic by, for example, injection molding and may have intermediate tolerances on the order of +/−10 □m. The purpose of the interposer 1400 is to provide a transition between the very small structures of the MEMS device 10 and the gross, macroscopic structures of the cartridge 1000 and reservoirs 20, 22 and 40. Accordingly, the cell sorting system 1 described herein may include a cell sorting valve 10 microfabricated on a surface of a silicon substrate, with microfabricated channels leading from the cell sorting valve 10, wherein the cell sorting valve 10 separates the target particles from non-target material, a disposable cartridge 1000 containing a sample reservoir 20, a sort reservoir 22 and a waste reservoir 40; and an interposer 1400 that provides fluid communication between the microfabricated channels in silicon substrate and the reservoirs in the disposable cartridge.

Because the interposer 1400 can be made with reasonably fine tolerances (+/−10 □m), it is possible to align the passages in the interposer 1400 with passages in the MEMS chip when the apertures to the channels are on the order of about 300 microns. While the widths of the channels leading to and from the movable valve 110 may be substantially smaller on the order of 150 microns, the apertures which introduce the fluid to the channels may be made near this scale. The apertures are shown in FIG. 6.

Figure 6:
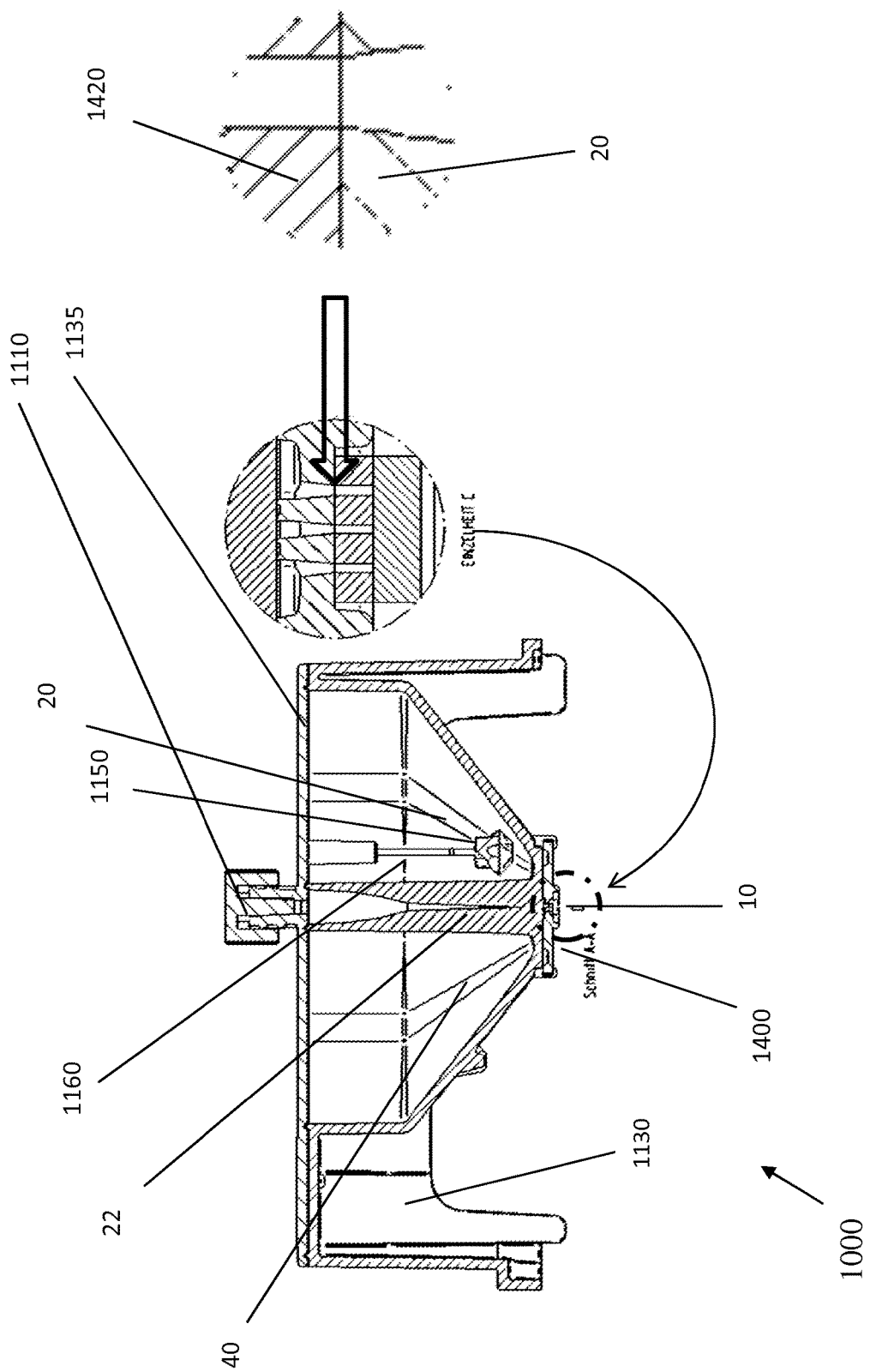
FIG. 6 is another side view of the exemplary disposable cartridge which may be used in the MEMS cell sorting system of FIG. 3, which includes a MEMS chip sorter and an interposer

As shown on the insert of FIG. 6, the through holes such as 1420 in interposer 1400 may have a tapered shape, with a diameter on the order of 300 microns at the top. This aperture may taper to a diameter of about 150 microns at the base where it meets the corresponding aperture of sort channel 20 of MEMS chip sorter 10.

FIG. 6 also illustrates the details of the mixing mechanism, which may include a propeller 1150 mounted on a rotating shaft 1160. The shaft may extend from the top surface of the cartridge 1135 through a bearing structure which allows the shaft to rotate freely. If the propeller 1150 contains magnetic components, the mixing action may be accomplished by a rotating magnetic field external to the cartridge 1000. The applied field my drive the motion of the propeller, causing it to rotate on the shaft 1160. Alternatively, a mechanical coupling may engage a motor which then rotates the shaft 1160. Accordingly, the cell sorting system 1 may include a disposable cartridge 1000, which may further include a propeller on a shaft, wherein the propeller 1150 is disposed in the sample reservoir 20. The propeller 1150 may comprise magnetic material, and which interacts with a variable magnetic field which turns the propeller 1150 on its shaft 1160, thereby mixing the contents of the sample reservoir 20. Alternatively, the cell sorting system 1 may include a propeller 1150 which is rotated by a mechanical coupling that rotates the shaft 1160, and is driven by a motor.

Figure 7:
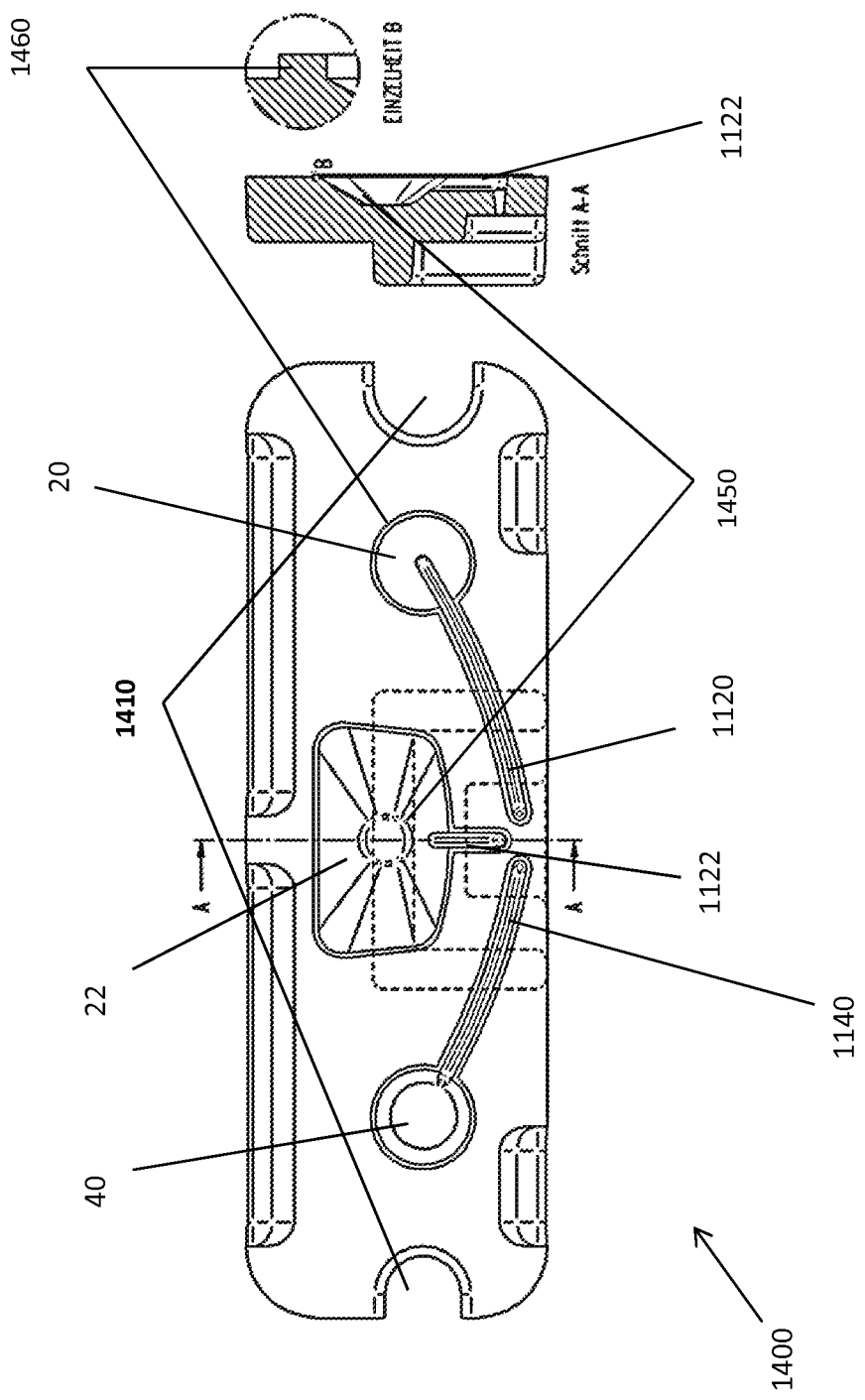
FIG. 7 is a plan view of an exemplary interposer which may be used with the disposable cartridge of FIG. 4.

The interposer 1400 may have passages formed therein, 1120, 1122 and 1140, shown in FIG. 7, which may correspond to channels 120, 122 and 140 shown in FIGS. 1 and 2. That is, passage 1120 may mate with passage 120 on MEMS chip sorter 10, to provide a fluidic pathway from sample reservoir 20 to MEMS chip sorter 10. Downstream of MEMS chip sorter 10, the interposer 1400 may provide a fluidic pathway from the movable valve 110 to the sort reservoir 22 (in cartridge) via sort channel 122 (on chip) and 1122 (on interposer). Similarly, the interposer 1400 may provide a fluidic pathway from the movable valve 110 to the waste reservoir 40 (in cartridge) via waste channel 140 (on chip) and 1140 (on interposer). In other words, the interposer 1400 may provide a sort fluid path between a sort reservoir 22 in the disposable cartridge 1000 and the sort channel 122 in the silicon substrate, a waste fluid path between a waste reservoir 40 in the disposable cartridge 1000 and the waste channel 140, and a sample fluid path between the sample channel 120 and a sample reservoir 20.

Another purpose of the interposer 1400 is to provide a collection region for possibly small volumes of sorted material. For example, since the target cells may be rare, such as stem cells, the volume of fluid collected in the sort reservoir 22 may also be rather small, and in proportion to the frequency of target cells in the sample. Accordingly, volumes as low as a few microliters may be expected. The interposer 1400 may provide a region into which the sorted effluent is siphoned, for easy collection with a small pipette. This siphon region 1450 is shown in FIG. 7.

In particular, it should be noticed that the floor of siphon region 1450 is at a lower elevation than the bottom of the sort channel 1122. Accordingly, fluid may flow as assisted by siphoning action and meniscus forces from the MEMS chip sorter 10 to the sort reservoir 22, from which it can be retrieved by hypodermic needle or micropipette. This siphoning may help offset the capillary forces that may occur from small volume flow in the very small channels. Accordingly, the sort reservoir 22 may further comprise a siphon structure that collects a smaller sort fluid volume within the sort reservoir 22, wherein the smaller sort fluid volume is less than about 10% of the total fluid volume of the sort reservoir 22.

Importantly, the sort channel 1122 may be made relatively short compared to sample channel 1120 and waste channel 1140, so that the amount of material lost by adhesion to channel walls, for example, is minimized.

Also shown in the detail of FIG. 7 is a glue dam 1460, which will be described next with respect to cartridge assembly.

As can be seen in FIG. 7, the sample channel 1122 may draw material from the very bottom of the sample reservoir 20. This may be important in maximizing the yield, or percent of recovered material, from a given sample volume. In contrast, the waste channel 1140 may deliver the non-target material to a point on the incline of the wall of the waste void or reservoir 40.

The interposer 1400 may be made from polycarbonate, polymethyl methacrylate (PMMA), or cyclic olefin polymer (COP), by injection molding, embossing, laser machining or 3D printing. The tolerances on the passages 1420 shown in FIG. 6 in the interposer 1400 may be about +/−10 microns on a total diameter of about 100 to 400 microns. The corresponding passages 20 in the MEMS chip sorter 10 may be about 50 to 150 microns. These passages 20 and 1420 may then be aligned as was shown in the insert to FIG. 6 to within about 10 microns. The interposer 1400 is affixed to the silicon substrate by any convenient adhesive, such as glue, epoxy and cement. The MEMS chip sorter 10 may first be glued to the interposer by seating it in the chip cavity 1470 shown in FIG. 9. The cavity 1470 may be formed sufficiently precisely that the passages in MEMS chip sorter 10 roughly overlap the passages in interposer 1400. The allowed mismatch may be up to about 20 microns, easily achievable. A pick and place machine, well known in printed circuit board manufacturing, may be adequate for this task. The MEMS chip sorter 10 may be glued in place within cavity 1470. Of course, the materials and methods described here are exemplary only. Other materials, such as other plastics, and other corresponding methods may be used.

Figure 8:
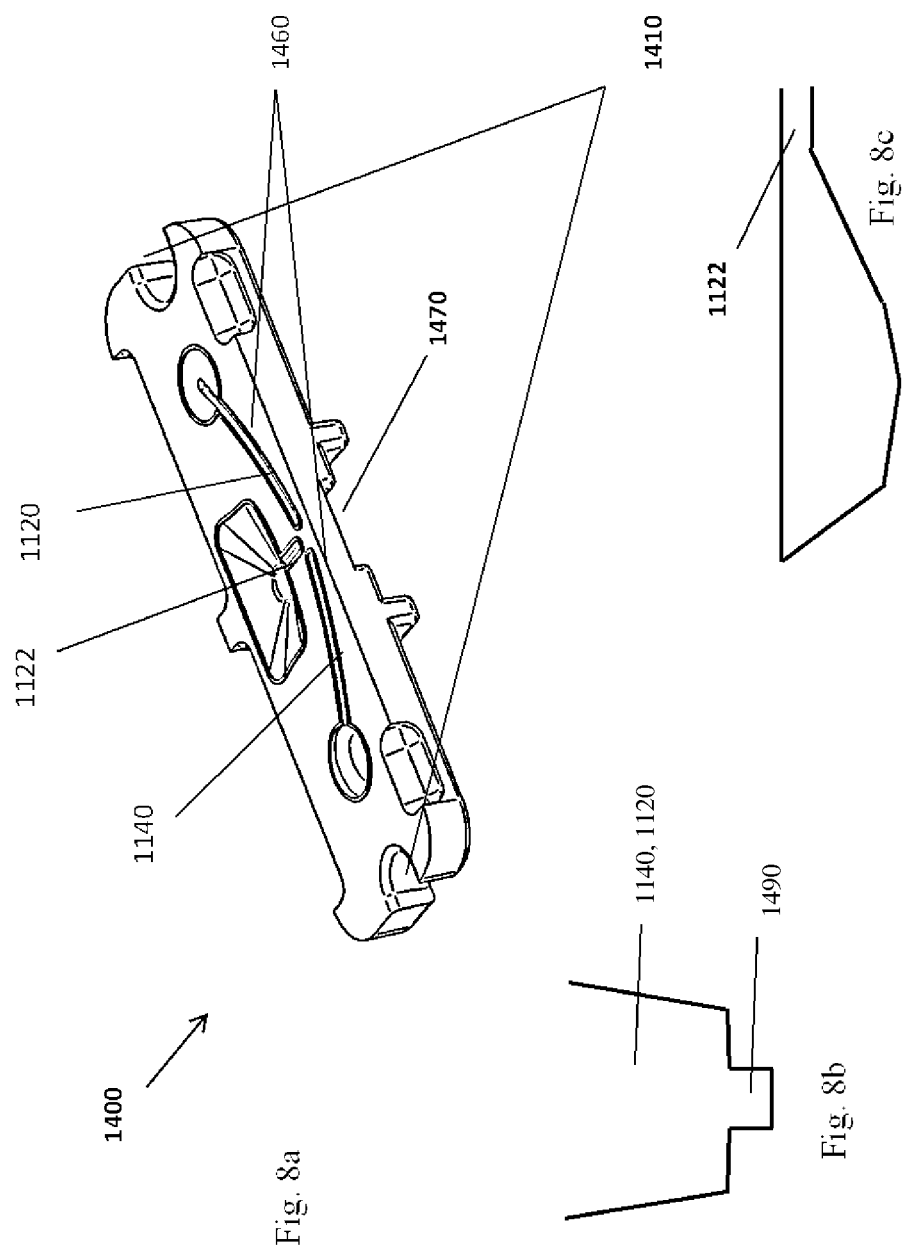
FIG. 8a is a perspective view of the exemplary interposer which may be used with the disposable cartridge of FIG. 4, showing the cartridge-facing side.
FIG. 8b is a cross sectional view of a channel.
FIG. 8c is a cross sectional illustration of another embodiment of a channel.

The interposer 1400 may then be installed in the cartridge base 1130 with glue or cement, by locating the interposer 1400 locating holes 1410 against corresponding posts in cartridge body 1000. Since this glue or cement will be required to be watertight, yet not interfere with passages 1120, 1122 or 1140, some features may be formed as glue dams 1460 around these channels, as shown in FIGS. 7 and 8. These glue dams 1460 may serve to keep the liquid, uncured glue from entering the small channels 1120, 1122 and 1140. The features 1460 may be raised ridges of plastic material which prevent the liquid from entering the channels or other depressions. In particular, glue may be injected into a port that gives access to the interface between interposer 1400 and the remainder of cartridge body 1000. The glue will wick around this area but may be kept out of microfluidic passageways 1120, 1140 and 1122 by glue dams 1460 that surround these passageways as shown in FIG. 7 and in the perspective drawing of FIG. 8. The glue dams reduce the thickness of the interface between interposer 1400 and the remainder of cartridge body 1000 from about 5 to 50 μm to 0.2 to 2 μm thereby creating a capillary effect that prevents the glue from flowing beyond the dam into the microfluidic passageways. It should be understood that these dimensions are exemplary only, and that such details will depend on the specifics of the application. Depending on the type of glue used, the liquid glue may be cured by heat, pressure or exposure to UV radiation, for example.

Figure 9:
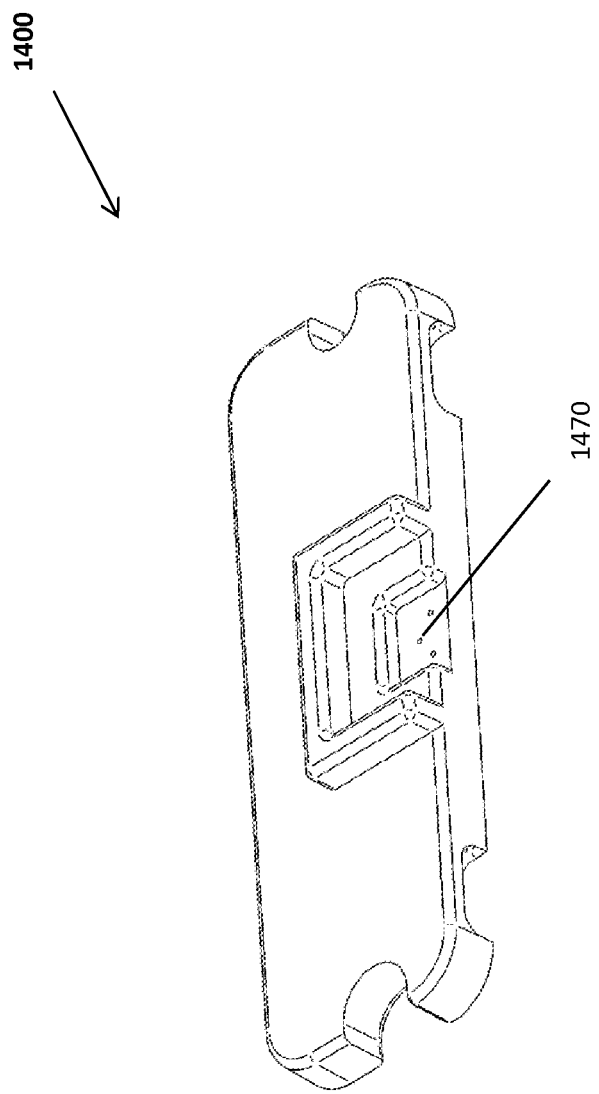
FIG. 9 is a perspective view of the obverse side of the exemplary interposer.

FIG. 9 is a simplified perspective view of the obverse side of the interposer 1400. This side includes the seating area 1470 for MEMS chip sorter 10. The MEMS chip sorter 10 may be glued or otherwise bonded against the features of seating area 1470

Exemplary dimensions for the interposer are 16 mm length, 6 mm width, 1 mm height. The waste and sample reservoirs may be 2 mm in diameter. The sample channel 1120, sort channel 1122 and waste channel 1140 may each be 300 microns in width. The height of the glue dams may be about 20 microns.

Accordingly, a manufacturing process for the cartridge 1000 may include:
1) Glue MEMS chip sorter 10 to interposer 1400
2) Place interposer 1400 against cartridge 1000 locating pins
3) Press interposer 1400
4) Introduce glue to gaps between interposer 1400 and cartridge 1000
5) UV cure glue
6) Attach cartridge base 1130 to cartridge top 1135 by glue, cement, or ultrasonic welding, for example
7) This invention relates to a cell sorting system using a microfabricated, movable cell sorting mechanism.

It should be clear that steps 1-6 need not be executed in the order shown. For example, the cartridge base 1130 may be attached to the cartridge top 1135 before attaching the MEMS chip 10 or interposer 1400.

In another embodiment of the cell sorting system, the disposable cartridge and/or the interposer further comprise at least one calibration region to calibrate the interrogation means.

Figure 10:
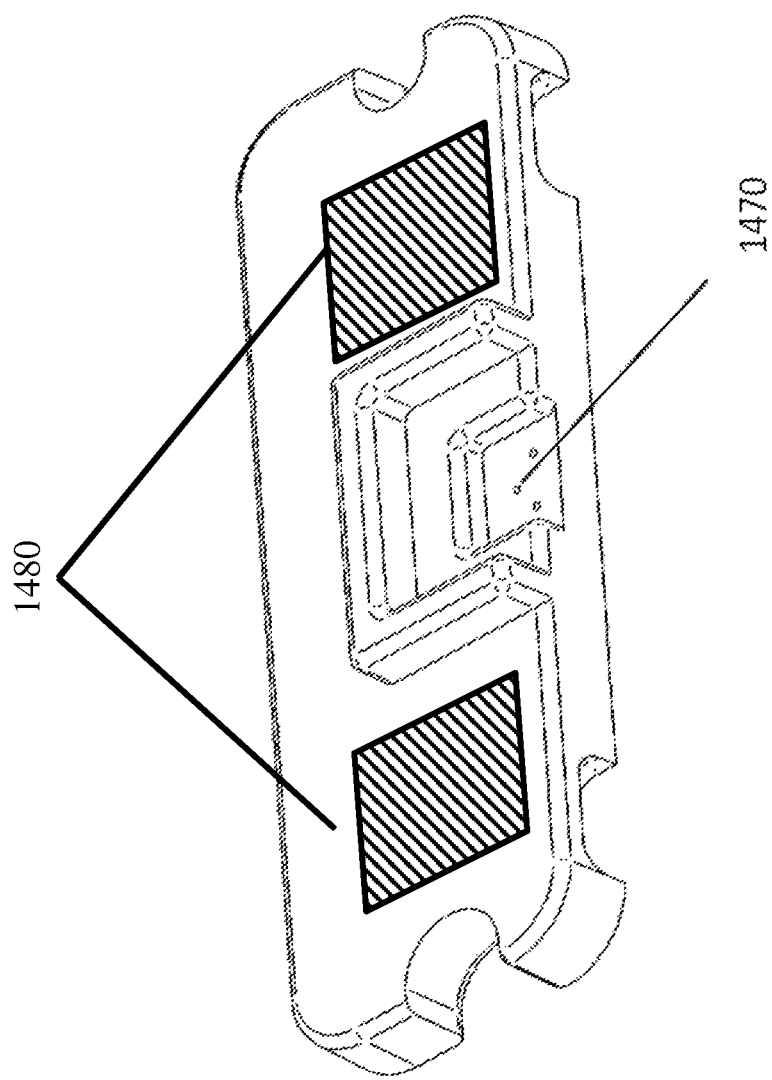
FIG. 10 is a perspective view of the obverse side of the exemplary interposer showing calibration areas.
Figure 11:
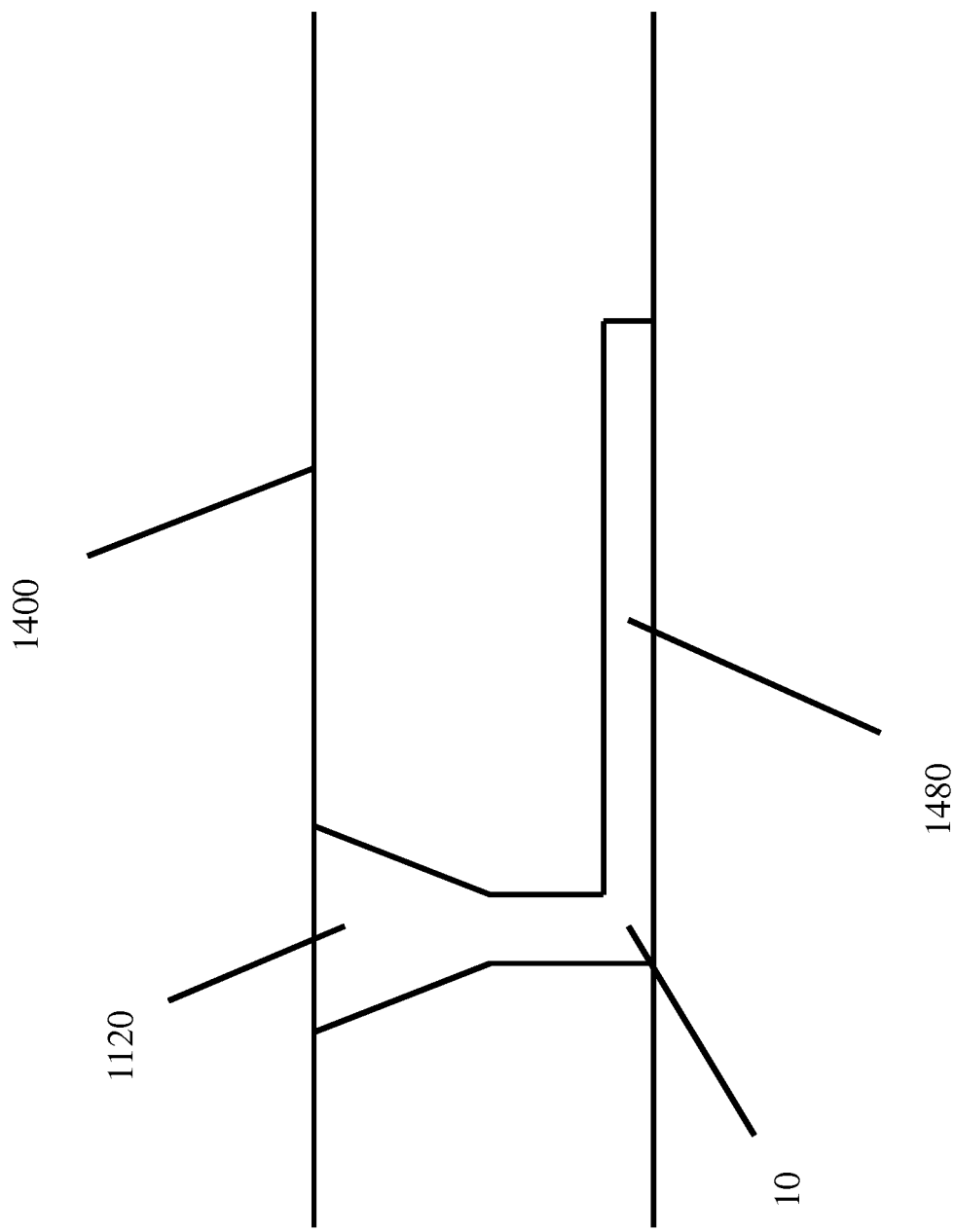
FIG. 11 is a cross sectional view of the interposer with calibration areas.

FIG. 10 is a simplified diagram of the interposer 1400 comprising calibration regions. The interposer 1400 may have areas 1480 that are used for calibration purposes. These areas 1480 may have particular, pre-defined optical or fluorescence properties that are used for the calibration or compensation of an optical system. Therefore, the areas 1480 can be made of one or more fluorescent material or one or more fluorescent material is added (printed) to these surfaces. Alternatively, microfluidic structures may be used to guide and store one or more fluorescent liquids to these calibration areas. The application of these fluorescent liquids may therefore take place at a different position on the interposer. FIG. 11 is a cross sectional view of such a variant of the interposer 1400 with calibration areas 1480. The interposer may have a sample channel 1120 as described above, which brings the sample fluid to the MEMS chip sorter 10. The fluid may then pass into the calibration areas 1480.

The calibration is meant to make sure suspended matter having equivalent fluorescent staining gets consistently detected across instruments and over time. This is achieved by measuring the intensity of a material with known fluorescence. Instead of using calibration particles in a different run, this may be achieved by illuminating and detecting fluorescence from the calibration area on or in the interposer within the cartridge. Calibration may be carried out any time, for example after inserting the cartridge in the system before starting the sorting process, or during a sorting process in order to control or maintain system performance.

By calibration against a known fluorescing material, a predefined target intensity can be adjusted by the system of the invention. Calibration can be performed several times in an iterative process and can be further utilized to characterize and validate system performance.

The fluorescing material used for the calibration area 1480 are selected that they can be detected in at least, one, at best all fluorescence detection channels used in the system and that their fluorescence intensity (absolute brightness) is at least in the same order of magnitude as the fluorescence intensity (absolute brightness) the material to be processed. Especially suitable as fluorescing material for the calibration area are Coumarin-6, Nile-Red and/or Bodipy-650.

In another embodiment of the invention, the fluid channel geometry of the interposer is designed to avoid trapping of bubbles and agglomeration of cellular material. Therefore, the channel geometries may be optimized with respect to fluidic properties. These features may minimize dead volumes, and avoid undercuts and rounded corners. Furthermore, the channel geometries at the interfaces to the chip and/or the cartridge main body may be designed in way that channel diameters are always increasing in flow direction. These design elements may also prevent the agglomeration of cellular material inside the fluidic channels.

Avoidance of trapped of bubbles can further be achieved by providing the channels in the interposer with a small channel at the bottom of the main channel ("channel-in-channel"). The small channel may have 5 to 20% of either the depth and/or with of the channel it is located in. FIG. 8b shows by way of example the a small channel 1490 at the bottom of a channel of the interposer, such as channels 1120 and 1140. A gas bubble blocking the main channel cannot enter the small channel due to surface tension and leaves the small channel open for flow of liquid. Another variant of avoiding trapped bubbles is shown in FIG. 8c, where channel 1122 leading to the siphon is shaped like a ramp leading into the siphon, thus avoiding sharp edges. Accordingly, the interposer may include least one channel having with an additional small channel disposed at the bottom of the at least one channel, wherein said small channel has between about 5 to about 20% of a depth and a width of the at least one channel.

Another aspect of the system described above with respect to FIGS. 1, 2 and 3 is the need for a precisely localized magnetic field which will actuate the small, MEMS chip sorter 10.

As described previously, the actuation mechanism in the system shown in FIG. 3 may be electromagnetic. Because the movable valve 110 is so small, it is important to have the flux-generating structure be precise, low power and efficient. Such a structure is shown in FIGS. 10a, 10b and 10c.

The external source of magnetic field lines (magnetic flux) may be provided outside the MEMS chip sorter 10, as was shown in FIGS. 2 and 3. This source may be an electromagnet 400. The electromagnet 400 may include a permeable core 470 around which coils 460 are wound. The coils 460 and core 470 generate a magnetic field which exits the pole of the magnet at the tip 450, diverges, and returns to the opposite pole, as is well known from elementary electromagnetism. In general, there may be a trade-off between fewer layers of coils 460 for more effective heat dissipation, or more layers for greater flux (Amp*turn), and thus greater force and higher speed. In one embodiment, the coils 460 have one layer, but the magnet body will often have at most three layers of coils 460. When the electromagnet 400 is brought into the vicinity of the movable valve 110, and the coil 460 is energized, the coil 460 and core 470 generate lines of flux that diverge rapidly from the tip 450. Accordingly, the movable member 110 is generally drawn toward the tip 450 of the electromagnet 400 as shown in FIG. 12a, because the permeable material is drawn into areas of increasing flux density.

As shown in FIG. 12a, the magnet 470 may be given a tapered shape, which may tend to further concentrate the magnetic flux in the region around the tip 450. The angle of the taper may be, for example, between about 0 and to about 30 degrees from vertical. The aspect ratio (length of taper/average width of taper) may be around 2/1 for example, but may be designed in a broad range of shapes. In order to focus the flux at the tip 450, however, it may be advantageous to have the diameter at the tip be less than the diameter at the base of the tapered shape. FIG. 12b is an enlarged view of the tip of electromagnet 400, showing the tapered shape of the tip, face-on. FIG. 12c is a perspective view of the tapered shape 450, coils 460 and magnet body 470.

Magnetic modeling suggests that a electromagnet tip of the approximate width of the permeable elements 116 in the MEMS chip sorter 10 is optimal, with a height of approximately the same order of magnitude. The base size is then determined by the taper angle. In one embodiment, the base of the tapered shape may have a length of 2 to 5 mm and a width of 0.5 to 2 mm. The tip of the tapered shape may be smaller than the base and have rectangular dimensions of about 1.0 mm×0.7 mm, or at least about 0.4 mm×0.2 mm. It should be understood that these dimensions are exemplary only, and that such details will depend on the specifics of the application.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. A cell sorting system for sorting target particles from a fluid sample, comprising:
    a cell sorting valve microfabricated on a surface of a silicon substrate, with microfabricated channels leading from the cell sorting valve, wherein the cell sorting valve separates the target particles from non-target material;
    a disposable cartridge containing a sample reservoir, a sort reservoir and a waste reservoir; and
    an interposer that provides fluid communication between the microfabricated channels in the silicon substrate and the reservoirs in the disposable cartridge and wherein the cell sorting valve moves in a plane parallel to the surface, and directs the target particles from the sample channel into the waste channel when the microfabricated cell sorting valve is in a first position, and which directs the non-target particles into the sort channel when in a second position, wherein the waste channel is substantially orthogonal to the plane of motion of the cell sorting valve.

2. The cell sorting system of claim 1, wherein the cell sorting valve directs the target particles from a sample channel into a sort channel formed in the silicon substrate and the non-target material from the sample channel to a waste channel also formed in the silicon substrate.

3. A cell sorting system for sorting articles from a fluid sample, comprising:
    a cell sorting valve microfabricated on a surface of a silicon substrate, with microfabricated channels leading from the cell sorting valve, wherein the cell sorting valve separates the target particles from non-target material;
    a disposable cartridge containing a sample reservoir, a sort reservoir and a waste reservoir; and
    an interposer that provides fluid communication between the microfabricated channels in the silicon substrate and the reservoirs in the disposable cartridge, wherein the cell sorting valve moves in a plane parallel to the surface, and directs the target particles from the sample channel into the waste channel when the microfabricated cell sorting valve is in a first position, and which directs the non-target particles into the sort channel when in a second position, wherein the sort channel and the waste channel are substantially antiparallel, and the sample channel and the waste channel are substantially orthogonal.

4. The cell sorting system of claim 3, wherein the interposer provides a sort fluid path between a sort reservoir in the disposable cartridge and the sort channel in the silicon substrate, a waste fluid path between a waste reservoir in the disposable cartridge and the waste channel, and a sample fluid path between the sample channel and a sample reservoir.

5. The cell sorting system of claim 4, wherein the sort reservoir further comprises a siphon structure that collects a smaller sort fluid volume within the siphon structure of the sort reservoir, wherein the smaller sort fluid volume is less than about 10% of a total fluid volume of the sort reservoir.

6. The cell sorting system of claim 4, wherein the sample reservoir further comprises a funnel-shaped feature formed in the wall of the sample reservoir, which collects a smaller volumes of sample fluid, wherein the smaller volume of sample fluid is less that about 10% of a total fluid volume of the sample reservoir.

7. The cell sorting system of claim 4, wherein the waste reservoir further comprises a funnel-shaped feature formed in the wall of the waste reservoir, which collects a smaller volume of waste fluid, wherein the smaller volume of waste fluid is less that about 10% of a total fluid volume of the waste reservoir.

8. The cell sorting system of claim 3, wherein the interposer is affixed to the silicon substrate by an adhesive, and installed in the disposable cartridge.

9. The cell sorting system of claim 3, wherein the cell sorting valve further comprises:
    a permeable magnetic material inlaid in the microfabricated cell sorting valve; and
    a first source of magnetic flux external to the microfabricated cell sorting valve and substrate on which the cell sorting valve is formed, wherein the magnetic flux interacts with the inlaid permeable magnetic material to move the microfabricated cell sorting valve, whereby the microfabricated cell sorting valve moves from the first position to the second position when the first source of magnetic flux is activated.

10. The cell sorting system of claim 3, wherein when the cell sorting valve is in the first position, a passage between the sample channel and the waste channel is formed.

11. The cell sorting system of claim 3, wherein when the microfabricated cell sorting valve is in the second position, a passage between the sample channel and the sort channel is formed.

12. The cell sorting system of claim 11, wherein the cell sorting valve moves from the first position to the second position in response to the application of a force.

13. The cell sorting system of claim 12, wherein the force is at least one of mechanical, electrostatic, magnetostatic, piezoelectric and electromagnetic.

14. The cell sorting system of claim 3, wherein the disposable cartridge further includes a propeller on a shaft wherein the propeller is disposed in the sample reservoir.

15. The cell sorting system of claim 14, wherein the propeller comprises magnetic material, and interacts with a variable magnetic field which turns the propeller on its shaft, thereby mixing the contents of the sample reservoir.

16. The cell sorting system of claim 14, wherein the propeller is rotated by a mechanical coupling that rotates the shaft, and is driven by a motor.

17. The cell sorting system of claim 3, further comprising:
    an interrogation means disposed in the sample channel, wherein the interrogation means distinguishes target particles from non-target materials in the sample stream.

18. The cell sorting system of claim 17, wherein the interrogation means comprises a laser in a laser-based, induced fluorescence system, wherein a fluorescent tag is affixed to the target particle, and emits a fluorescent signal when irradiated by the laser.

19. The cell sorting system of claim 3, wherein the disposable cartridge is configured to be accepted into the cell sorting system on a positionable stage, on which it can be positioned with respect to at least one laser source, and at least one optical detector.

20. The cell sorting system of claim 19, wherein the cell sorting system further includes a computer which is in communication with the at least one laser source, at least one optical source and the cell sorting valve, to separate the target particles from the non-target material.

21. The cell sorting system of claim 17, wherein the disposable cartridge further comprises at least one calibration region to calibrate the interrogation means.

22. The cell sorting system of claim 17, wherein the interposer further comprises at least one calibration region to calibrate the interrogation means.

23. A cell sorting system for sorting target particles from a fluid sample, comprising:
- a cell sorting valve microfabricated on a surface of a silicon substrate, with microfabricated channels leading from the cell sorting valve, wherein the cell sorting valve separates the target particles from non-target material;
- a disposable cartridge containing a sample reservoir, a sort reservoir and a waste reservoir; and
- an interposer that provides fluid communication between the microfabricated channels in the silicon substrate and the reservoirs in the disposable cartridge, wherein the interposer comprises at least one channel having an additional small channel disposed at the bottom of the at least one channel, wherein said small channel has between about 5 to 20% of a depth and a width of the at least one channel.

* * * * *